US011123540B2

(12) United States Patent
Mohl

(10) Patent No.: US 11,123,540 B2
(45) Date of Patent: Sep. 21, 2021

(54) DEVICE TO ASSIST THE PERFORMANCE OF A HEART

(71) Applicant: Miracor Medical SA, Vienna (AT)

(72) Inventor: Werner Mohl, Altenmarkt-Thennenberg (AT)

(73) Assignee: Miracor Medical SA, Vienna (AT)

( * ) Notice: Subject to any disclaimer, the term of this patent is extended or adjusted under 35 U.S.C. 154(b) by 98 days.

(21) Appl. No.: 16/282,948

(22) Filed: Feb. 22, 2019

(65) Prior Publication Data

US 2019/0184080 A1 Jun. 20, 2019

Related U.S. Application Data

(60) Continuation of application No. 14/454,965, filed on Aug. 8, 2014, now Pat. No. 10,251,984, which is a
(Continued)

(30) Foreign Application Priority Data

Feb. 27, 2007 (AT) .................................. A 306/2007

(51) Int. Cl.
*A61M 60/405* (2021.01)
*A61M 60/40* (2021.01)
(Continued)

(52) U.S. Cl.
CPC .......... *A61M 60/40* (2021.01); *A61M 60/135* (2021.01); *A61M 60/148* (2021.01);
(Continued)

(58) Field of Classification Search
CPC .. A61M 1/101; A61M 1/1015; A61M 1/1008; A61M 1/1031; A61M 1/1032;
(Continued)

(56) References Cited

U.S. PATENT DOCUMENTS 4,674,518 A 6/1987 Salo
5,308,319 A 5/1994 Ide et al.
(Continued)

FOREIGN PATENT DOCUMENTS

EP 0 075 606 4/1983
EP 0 503 839 9/1992
(Continued)

OTHER PUBLICATIONS

Authorized Officer Malte Kaden, International Search Report for Application No. PCT/IB2008/000421, dated Nov. 7, 2008, 3 pages.
(Continued)

*Primary Examiner* — Tammie K Marlen
(74) *Attorney, Agent, or Firm* — Fish & Richardson P.C.

(57) ABSTRACT

In a catheter (2) to assist the performance of a heart (1) with at least one pump (7), the pump is formed as a rotary pump at the distal end of the catheter (2), the rotor (6) lying distally on the outer side being coupled via a magneto coupling with a drive wheel (21), formed as a hydraulically or pneumatically operated paddle wheel, arranged inside the catheter (2). The driving fluid is supplied to the paddle wheel via a lumen (22) of the catheter (2) and is carried off via a further lumen (23) of the catheter.

13 Claims, 3 Drawing Sheets

Related U.S. Application Data continuation of application No. 13/555,318, filed on Jul. 23, 2012, now Pat. No. 8,801,590, which is a division of application No. 12/449,632, filed as application No. PCT/IB2008/000421 on Feb. 27, 2008, now Pat. No. 8,255,050.

(51) Int. Cl.

| | | |
|---|---|---|
| *F04D 13/02* | (2006.01) | |
| *A61M 60/135* | (2021.01) | |
| *A61M 60/148* | (2021.01) | |
| *A61M 60/205* | (2021.01) | |
| *A61M 60/422* | (2021.01) | |
| *A61M 60/857* | (2021.01) | |
| *A61M 60/414* | (2021.01) | |
| *A61M 60/833* | (2021.01) | |

(52) U.S. Cl.
CPC ........ *A61M 60/205* (2021.01); *A61M 60/405* (2021.01); *A61M 60/422* (2021.01); *A61M 60/857* (2021.01); *F04D 13/027* (2013.01); *A61M 60/414* (2021.01); *A61M 60/833* (2021.01)

(58) Field of Classification Search
CPC .. A61M 1/1036; A61M 1/1029; A61M 1/122; A61M 1/125; A61M 60/40; A61M 60/405; A61M 60/148; A61M 60/135; A61M 60/422; A61M 60/857; A61M 60/205; A61M 60/833; A61M 60/414; F04D 13/027
See application file for complete search history.

(56) References Cited

U.S. PATENT DOCUMENTS

| | | | |
|---|---|---|---|
| 5,449,342 A | 9/1995 | Hirose et al. | |
| 5,470,208 A | 11/1995 | Kletschka | |
| 5,964,694 A | 10/1999 | Siess et al. | |
| 6,007,478 A | 12/1999 | Siess et al. | |
| 6,083,260 A | 7/2000 | Aboul-Hosn | |
| 6,155,969 A | 12/2000 | Schima et al. | |
| 6,176,848 B1 | 1/2001 | Rau et al. | |
| 6,506,146 B1 | 1/2003 | Mohl | |
| 6,508,787 B2 | 1/2003 | Erbel et al. | |
| 6,540,658 B1 | 4/2003 | Faschiano | |
| 6,623,475 B1 | 9/2003 | Siess | |
| 7,699,586 B2 | 4/2010 | LaRose et al. | |
| 8,255,050 B2 | 8/2012 | Mohl | |
| 9,616,157 B2 * | 4/2017 | Akdis | A61M 1/101 |
| 2008/0214888 A1 | 9/2008 | Ben Shalom | |
| 2011/0238172 A1* | 9/2011 | Akdis | F04D 13/0666 623/3.11 |

FOREIGN PATENT DOCUMENTS

| | | |
|---|---|---|
| EP | 1 011 753 B1 | 6/2000 |
| EP | 1 034 808 | 9/2000 |
| FR | 1 187 249 | 8/1959 |
| WO | WO 97/37698 | 10/1997 |
| WO | WO 99/15213 | 4/1999 |
| WO | WO 00/44417 | 8/2000 |

OTHER PUBLICATIONS

Mohl et al., "Intermittent Pressure Elevation of the Coronary Venous System as a Method to Protect Ischemic Myocardium," *Interactive CardioVascular and Thoracic Surgery*, vol. 4, 2005, pp. 66-69.

Syeda et al., "The Salvage Potential of Coronary Sinus Interventions: Meta-Analysis and Pathophysiologic Consequences," *The Journal of Thoracic and Cardiovascular Surgery*, vol. 127, No. 6 (Jun. 2004), pp. 1703-1712.

\* cited by examiner

DEVICE TO ASSIST THE PERFORMANCE OF A HEART

CROSS-REFERENCE TO RELATED APPLICATIONS

This application is a continuation of and claims priority to U.S. application Ser. No. 14/454,965 (now U.S. Pat. No. 10,251,984), filed on Aug. 8, 2014, which is a continuation of and claims priority to U.S. application Ser. No. 13/555,318 (now U.S. Pat. No. 8,801,590), filed on Jul. 23, 2012, which is a divisional of and claims priority to U.S. application Ser. No. 12/449,632 (now U.S. Pat. No. 8,255,050), filed on Aug. 18, 2009, which is the U.S. national phase of International Application PCT/IB2008/000421, filed on Feb. 27, 2008, which designated the U.S. and claims benefit of AT A 306/2007, filed Feb. 27, 2007, the entire contents of these prior applications are hereby incorporated by reference.

FIELD

The invention relates to a catheter to assist the performance of a heart with at least one pump.

BACKGROUND

After a heart failure, for example a cardiac infarction or other reasons for the decrease in the performance of a heart, it is of essential importance for intensive care medicine to normalise and stabilise the cardiac function again as rapidly as possible. When for example the volume output of the heart is distinctly reduced as a result of a failure, it is particularly important to reliably and rapidly re-establish a corresponding peripheral blood flow in order to prevent secondary damage. The use of heart-lung machines basically allows the essential vital functions to be maintained. A specific adaptation to the respective actual requirements generally does not take place with such devices, however. Rather, conventional heart-lung machines are devices which, using external pumps, maintain a forced circulation of blood without systematically entering into the respective requirements of the heart which has been weakened or subjected to a failure.

In surgical interventions, particularly in the vein area, it has already been proposed to carry out retroinfusion, controlled by venous pressure, from or in veins of the body with the suction" of fluid and return of the fluid via a pump. Conventional catheters are used here, the lumina of which allow a suction of fluid and via the lumina of which the return is made possible at a suitable site. Known devices, particularly for the retroinfusion of blood in coronary veins in the area of myocardial protection during a brief coronary artery closure within a cardiological intervention, are generally devised so that a balloon dilatation of an arteriosclerotically constricted coronary artery is carried out. In these cases, a compensation which is adapted to the intervention briefly taking place respectively can be carried out by the return of blood which has been drawn off in veins. For a continuous restitution of the full function of a heart, however, the criteria are not taken into account which would be relevant for the full function of the heart, and an intensive provision over a particular period of time is therefore not provided with such devices. At the same time, the provision of the other organs must also be maintained.

In the device known from AT 407 960 B for assisting the performance of a heart, fluid is removed from blood vessels via an external pump and is returned into blood vessels via a return catheter, in which the returned quantity of fluid is regulated as a function of measurement values, with a heart ventricle catheter being provided to obtain these measurement values. The known device comprised a heart ventricle catheter which is equipped in the cardiac chamber with sensors to measure the volume of fluid per unit of time, in which these sensors, in the introduced state of the heart ventricle catheter, lie in the cardiac chamber and these sensors are connected with an evaluation circuit in which the ratio of the diastolic volume to the systolic volume is evaluated per heartbeat or per unit of time in particular the discharge rate and/or the deviation of the volume conveyed per unit of time by the heart from a defined rated value is evaluated, for example the rated value, calculated from physically specific data for the cardiac output. The signal which is generated in this way is passed to the pump, via which fluid is withdrawn from the cardiac chamber and is recirculated as a function of the generated signal.

SUMMARY

The invention now aims to further develop this known device to the effect that an external pump can be dispensed with and, at the same time, the desired pressure increase can be brought into effect systematically at particular locations. In particular, the fluid flow which is improved by the pump is to be developed in a way in which the mechanical stress of highly sensitive fluids, such as blood for example, can be kept as low as possible and nevertheless the corresponding improvement to circulation can be ensured at desired locations. To solve this problem, the initially mentioned device of the catheter according to the invention, which can be used within the scope of the device described above, consists substantially in that the pump is constructed as a rotary pump at the distal end of the catheter, in which the rotor lying distally on the outside is coupled via a magneto coupling with a drive wheel which is arranged inside the catheter and is formed as a paddle wheel which is operated hydraulically or pneumatically and the driving fluid is supplied to the paddle wheel via a lumen of the catheter and is carried off via a further lumen of the catheter. Such an axial pump, which is directly connected with the catheter, can be brought with the catheter directly into the desired position and, at the same time, can be used here with further therapeutic additions such as, for example, a retroper-fusion through cyclic occlusion of the blood vessel by means of a balloon. In order to guarantee a complete uncoupling from the driving medium driving the pump and in particular to ensure that simple driving means such as, for example, hydraulically or pneumatically operated paddle wheels can be used, a completely impervious separate on of the rotor from the drive wheel is achieved by the magneto coupling which is provided according to the invention, which eliminates axial passages between the drive wheel and the rotor lying distally on the outside. The embodiment is hereby devised according to the invention so that the drive wheel is formed as a hydraulically or pneumatically operated paddle wheel, with the driving fluid being supplied to the paddle wheel via a lumen of the catheter and being carried off via a further lumen of the catheter, in which preferably the paddle wheel is constructed with axial or semi-axial blades. The operation of such an arrangement can take place in a simple manner by means of correspondingly regulated hydraulic or pneumatic reservoirs, with the driving medium being supplied via corresponding regulating valves to the drive wheel which is coupled magnetically with the rotor.

The device is designed in a structurally particularly simple manner such that the axis of rotation of the rotor is in alignment with the longitudinal axis of the catheter or is parallel thereto. A development of the catheter which has a correspondingly low wear and is impervious, with, at the same time, a secure mounting of the rotor, can be achieved in that the coupling is formed by bar magnets which, in adjacent chambers separated from each other hydraulically by a sealing wall, at the distal end of the catheter are respectively connected with the rotor and with the drive wheel so as to be locked against relative rotation, in which preferably the connections: locked against relative rotation, of the drive wheel or of the rotor with the respective bar magnets are respectively mounted in the walls of the chambers facing away from the sealing wall and facing the drive wheel or the rotor respectively.

The rotor itself can follow design principles such as described for example in WO 01/70300 A1. The rotary pump shown and described there for conveying blood and other highly sensitive fluids is formed as an external electromagnetically driven pump which is not directly suitable for incorporation into a catheter. The known design namely assumes that centrifugal flow components and flow components directed against a housing are present, in which the flow components directed against the housing serve primarily for the non-contact mounting and stabilizing of the rotor in the housing. However, with an arrangement of the rotor at the distal end of a catheter, a closed housing can not be readily realised with regard to flow technology, because such housing walls must in fact lie at a precisely defined distance from the rotor, which, however, is not readily guaranteed at the distal end of a catheter. However, for the desired conveying capacity with the axial pump according to the invention, provision is also made according to the invention that the rotor has guide surfaces to produce centrifugal flow components.

The driving fluid can be used within the scope of the invention in order to be able to operate a balloon for retroperfusion. The embodiment is preferably devised hereby so that the lumina for the driving fluid are guided through an expandable balloon surrounding the catheter in a sealing manner, and that the lumina have separately controllable closure members via which driving fluid can arrive in the balloon or out of the balloon into the respective lumina, in which preferably the closure members are formed as magneto valves. On inflation of the balloon, additional driving medium is required which can be discharged again on collapsing of the balloon. This is possible extracorporally on the drive side by means of a reservoir.

The embodiment to assist the performance of a heart according to the invention, in which fluid is conveyed in blood vessels with the use of a pump and the conveyed quantity is able to be regulated as a function of measurement values of a heart ventricle catheter, from which the cardiac output is determined, proceeds from a development according to AT 407 960 B and is characterised substantially in that the pump is formed as an intravasal rotary pump at the periphery or at the distal end of the catheter, the rotor of which, lying on the outside, is connected via a magneto coupling with the drive which is arranged inside the catheter.

BRIEF DESCRIPTION OF DRAWINGS

The invention is explained in further detail below by use of an examplary embodiment which is illustrated diagrammatically in the drawings, in which.

DETAILED DESCRIPTION

Figure 1:
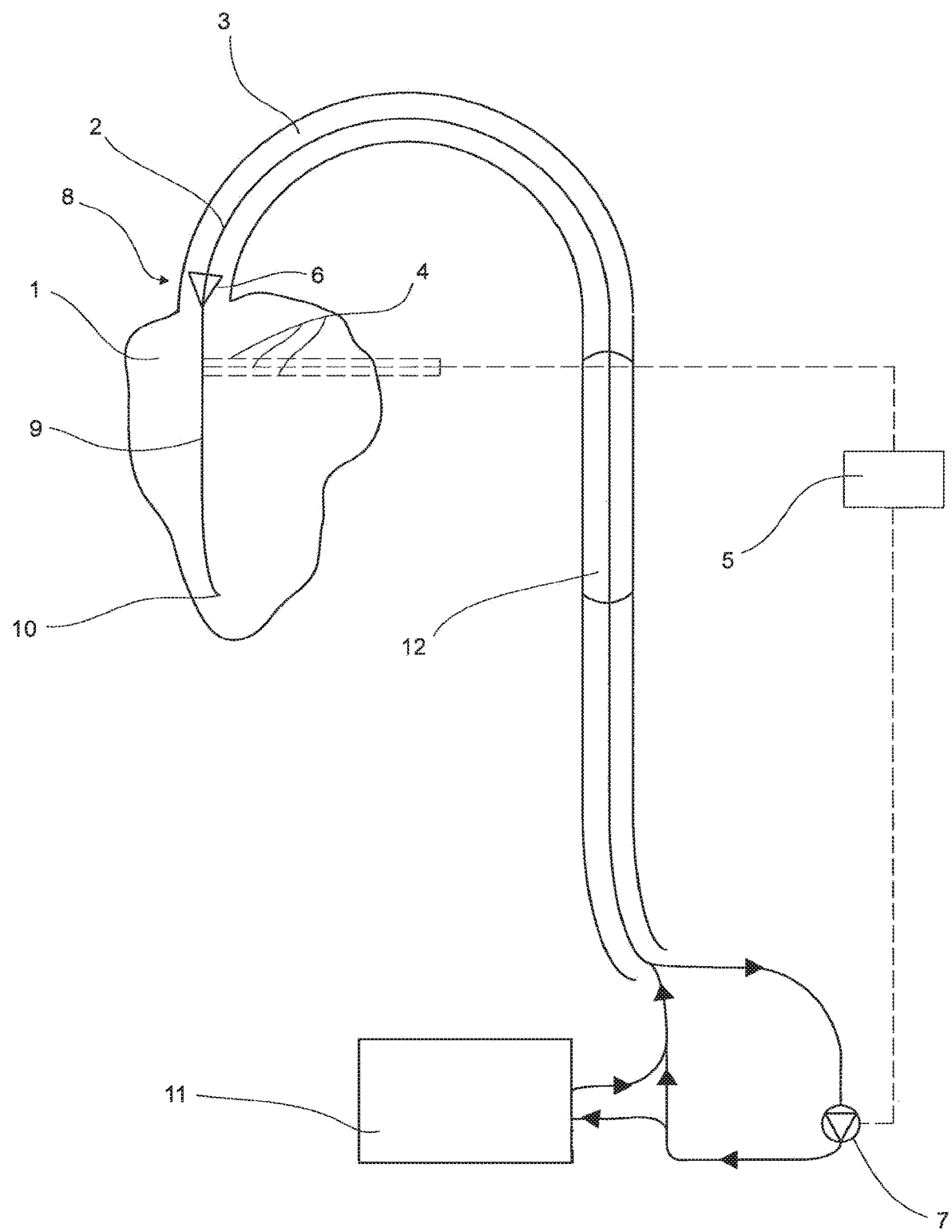
FIG. 1 shows a diagrammatic illustration of the arrangement of the pump and of the drive.

In FIG. 1, a heart is designated by 1, into which a heart ventricle catheter 2 is introduced. The catheter is introduced here for example via the femoral artery and the aortic arch 3 into the heart chamber and carries a series of sensors 4 via which the volume can be determined. The measurement signals are passed to a control arrangement 5. The heart ventricle catheter is formed with several lumina, as additionally illustrated below in further figures of the drawings, with fluid being supplied via such lumina to drive a rotor, arranged at the distal end, which forms the pump to assist the blood circulation and is designated by 6 in FIG. 1. The positioning of this rotor is indicated in FIG. 1 by the arrow 8. The driving medium for the rotor or the pump is guided in a circular flow by means of a fluid pump 7 which can be regulated in a synchronised manner as a function of the control signals generated in the control arrangement 5. The distal region in which the pump is arranged is designated diagrammatically by 8, the catheter 2 having at its distal end a tube 9 leading to the suction end 10. A reservoir for driving fluid is designated by 11, which provides additional driving medium for filling the balloon 12 serving for an occlusion of the artery, and which receives again the volume of driving medium occurring on deflation of the balloon.

The volumetric measurement in the cardiac chamber allows differences to be reliably detected between the diastolic and systolic volume and allows corresponding correction signals to be made available for the output of the synchronised fluid pump 7. Furthermore, in the control circuit 5, corresponding fixed values can be provided, such as for example a defined cardiac output, which is referred to on deviation of the measured cardiac output to control the pump.

A retroperfusion can take place via a conventional balloon catheter which is occluded in a correspondingly synchronized manner, so that the directed return is in fact guaranteed during the diastole. Hereby the corresponding measurement values for the heart rate or for the correct moment of the diastole can be obtained from ECG data.

Figure 2:
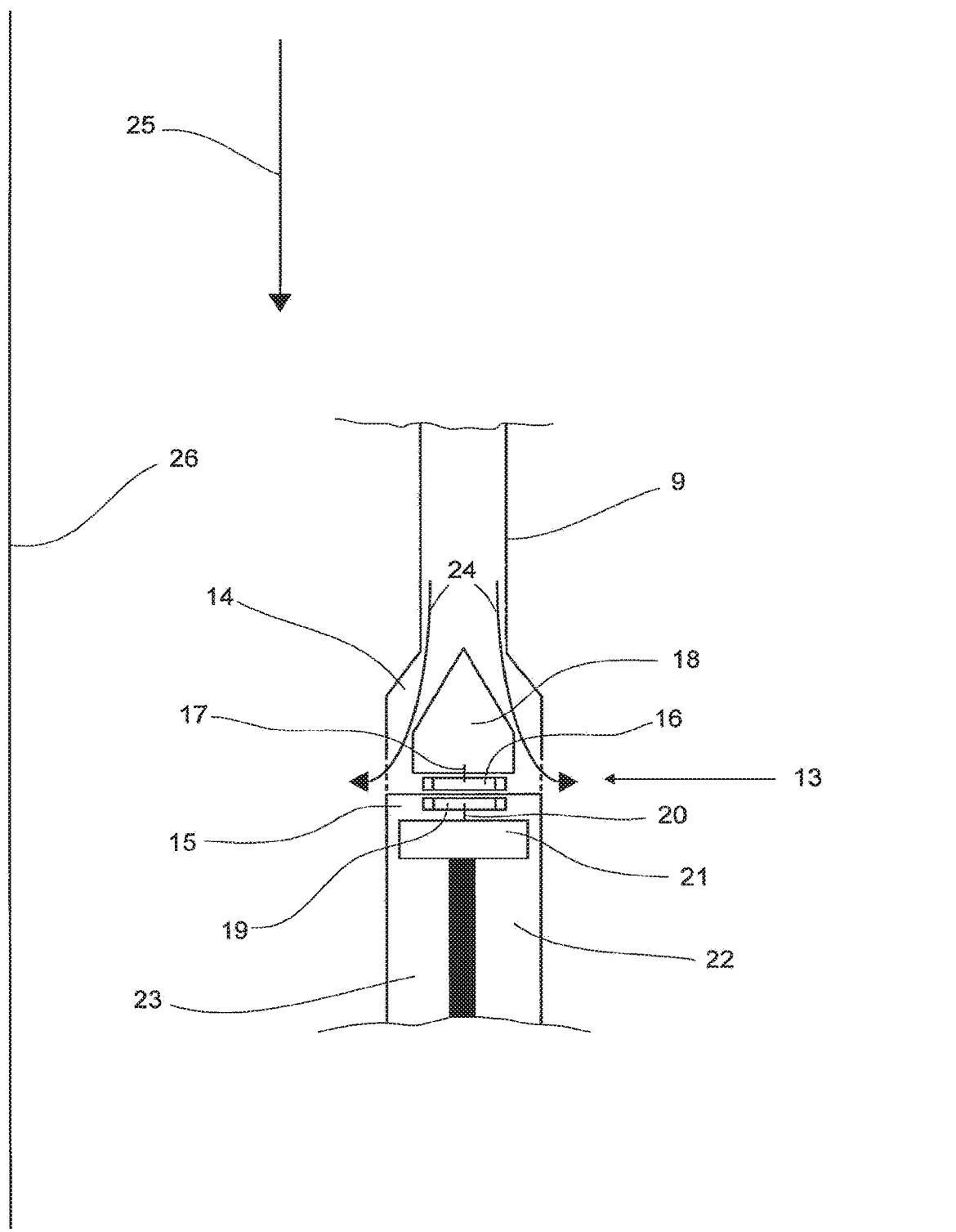
FIG. 2 shows a diagrammatic illustration of the distal end of a catheter which is used according to the invention.

In FIG. 2, the distal end of a modified catheter 2 is now illustrated. The end side 13 of this catheter has two pocketshaped chambers 14 and 15, in which bar magnets are respectively arranged. The bar magnet 16 is connected here at the distal end outwards via a shaft 17 with a rotor 18, whereas the bar magnet 19 lying on the inside is connected via a shaft 20 with a drive wheel 21. The drive wheel 21 is formed here as a paddle wheel and is acted upon with fluid via a lumen 22, this fluid flowing off again via the lumen 23 of the catheter. The rotation of the paddle wheel 21 is regulated here accordingly by corresponding control of the fluid pressure in the lumen 22 serving for the supply of fluid, in which the magnet 19, which is connected so as to be locked against relative rotation with the paddle wheel 21, is set into corresponding rotation. At the outer side, which is completely sealed with respect to the lumina 22 and 23, the magnet 16 is subsequently entrained accordingly and drives the rotor 18 via the shaft 17, whereby a flow is formed in the region of the tube 9, as is indicated by the arrows 24, and which assists the natural blood flow in the vessel 26, illustrated by the arrow 25.

Figure 3:
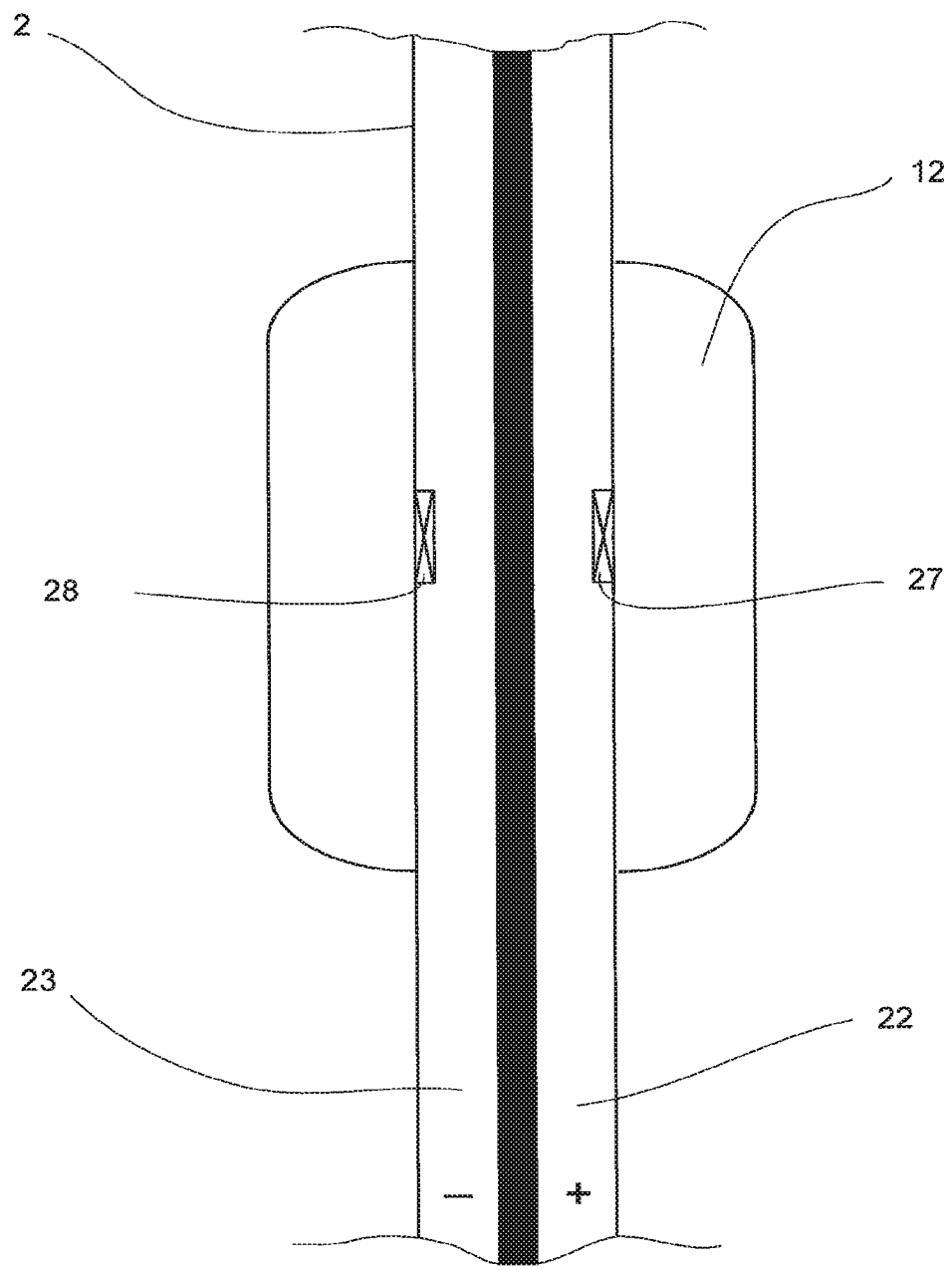
FIG. 3 shows an enlarged illustration of the part of the catheter bearing the balloon, in section.

In FIG. 3, the partial region of the balloon 12, which is connected in a sealing manner to the catheter 2, is illustrated on an enlarged scale. The two lumina leading away from the fluid pump 7 and back to the fluid pump 7 are designated in turn by 22 and 23. In the region of the balloon 12, the wall of these lumina is provided with valves which can be actuated magnetically for example. The valves are indicated diagrammatically by 27 and 28. An opening of the valve 27 leads to the fluid, coming from the fluid pump 7, which is under pressure, which is indicated by the "+" sign, being pumped into the balloon 12, with which the overall quantity of the circulating driving fluid would of course be reduced, in so far as the reservoir 11, indicated diagrammatically in FIG. 1, is not provided. By closing the valve 27, the occlusion is closed off, the collapsing of the balloon 12 being able to be brought about by opening the valve 28 and the fluid now being drawn off via the lumen 23, leading back to the pump, which lumen 23 is at a slightly lower pressure which is indicated by the "−" sign. As the overall volume of the fluid in the circulating system is now to be reduced, a portion of this volume must be pumped back again into the reservoir 11 according to FIG. 1.

The invention claimed is:

1. A system for assisting the blood circulation of a heart, comprising:
    a heart assist pump device deliverable to the heart and comprising:
        an inflow tube defining a blood inflow path;
        a magnetically driven rotor axially aligned with the inflow tube and that is rotatable within a surrounding rotor housing to act upon blood flowing from the inflow tube toward the rotor, the rotor being rotatable about a central axis and being rigidly coupled to a first magnetic device;
        a second magnetic device axially aligned with the inflow tube and positioned to magnetically drive rotation of the magnetically driven rotor via a magneto coupling with the first magnetic device while being spaced apart and sealed from the magnetically driven rotor, the surrounding rotor housing, the first magnetic device, and the inflow tube;
        a blood outflow port positioned radially adjacent the magnetically driven rotor such that blood driven by the magnetically driven rotor exits the surrounding rotor housing in a direction substantially perpendicular from the blood inflow path and the central axis of the magnetically driven rotor, wherein the magneto coupling orients the magnetically driven rotor so that the magnetically driven rotor remains adjacent to and spaced apart from the surrounding rotor housing by the blood flowing from the inflow tube and to the blood outflow port; and
    an external control unit configured to regulate operation of the second magnetic device, the external control unit being positionable exterior to a body when the heart assist pump device is delivered to the heart, wherein the external control unit is connectable to the heart assist pump device for operating the second magnetic device to thereby magnetically drive the rotation of the magnetically driven rotor via the magneto coupling with the first magnetic device.

2. The system of claim 1, wherein the magnetically driven rotor comprises guide surfaces to produce centrifugal flow components.

3. The system of claim 2, wherein the heart assist pump device further comprises a sealing wall positioned between the second magnetic device and the magnetically driven rotor.

4. The system of claim 2, wherein the magnetically driven rotor is sealed from the second magnetic device and a drive source that regulates the operation of the second magnetic device.

5. The system of claim 4, wherein the drive source comprises a hydraulically or pneumatically operated paddle wheel activated by the external control unit.

6. The system of claim 1, wherein the heart assist pump device is formed as an intravasal rotary pump.

7. The system of claim 1, wherein the first magnetic device comprises a bar magnet.

8. The system of claim 1, wherein the second magnetic device comprises a bar magnet.

9. The system of claim 1, wherein the entirety of the magnetically driven rotor is spaced apart from the surrounding rotor housing by a gap which is occupied by the blood.

10. The system of claim 9, further comprising one or more sensors that deliver heart measurement signals to the external control unit.

11. The system of claim 10, wherein the external control unit is connectable to the heart assist pump device to deliver energy to the second magnetic device.

12. The system of claim 11, wherein the external control unit delivers energy to the second magnetic device via delivery of a driving fluid.

13. The system of claim 11, wherein the external control unit receives fixed values for a defined cardiac output for regulating operation of the second magnetic device.

* * * * *

UNITED STATES PATENT AND TRADEMARK OFFICE
CERTIFICATE OF CORRECTION

PATENT NO. : 11,123,540 B2
APPLICATION NO. : 16/282948
DATED : September 21, 2021
INVENTOR(S) : Werner Mohl Page 1 of 1

It is certified that error appears in the above-identified patent and that said Letters Patent is hereby corrected as shown below:

In the Claims

In Column 6, Line 28, Claim 6, please replace "intravasal" with -- intravascular --.

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*